United States Patent

Kwetkat et al.

[11] Patent Number: 6,156,721
[45] Date of Patent: Dec. 5, 2000

[54] USE OF ANIONIC GEMINI TENSIDES IN FORMULATIONS FOR WASHING, CLEANING AND BODY CARE AGENTS

[75] Inventors: Klaus Kwetkat, Lünen; Michael Brock, Schermbeck; Herbert Koch, Dorsten, all of Germany

[73] Assignee: RWE-DEA Aktiengesellschaft fuer Mineraloel und Chemie, Germany

[21] Appl. No.: 09/171,703

[22] PCT Filed: Mar. 14, 1997

[86] PCT No.: PCT/EP97/01298

§ 371 Date: Oct. 23, 1998

§ 102(e) Date: Oct. 23, 1998

[87] PCT Pub. No.: WO97/40124

PCT Pub. Date: Oct. 30, 1997

[30] Foreign Application Priority Data

Apr. 23, 1996 [DE] Germany .................. 196 16 096

[51] Int. Cl.$^7$ .................. C11D 1/18; C11D 1/20
[52] U.S. Cl. .................. 510/494; 510/119; 510/127; 510/130; 510/156; 510/290; 510/340; 510/351; 510/352; 510/357; 510/426; 510/502
[58] Field of Search .................. 510/130, 119, 510/426, 502, 127, 156, 290, 340, 351, 352, 357, 494

[56] References Cited

U.S. PATENT DOCUMENTS

| | | | |
|---|---|---|---|
| 3,557,039 | 1/1971 | McIntyre et al. | 260/29.2 |
| 3,959,230 | 5/1976 | Hays | 260/75 |
| 4,000,093 | 12/1976 | Nicol et al. | 252/529 |
| 4,427,557 | 1/1984 | Stockburger | 252/8.7 |
| 4,537,706 | 8/1985 | Severson, Jr. | 252/545 |
| 4,622,378 | 11/1986 | Gosselink | 528/66 |
| 4,634,551 | 1/1987 | Burns et al. | 252/102 |
| 4,676,921 | 6/1987 | Vander Meer | 252/174.23 |
| 4,711,730 | 12/1987 | Gosselink et al. | 252/8.75 |
| 4,795,584 | 1/1989 | Ross et al. | 252/174.23 |
| 4,968,451 | 11/1990 | Scheibel et al. | 252/549 |
| 5,142,020 | 8/1992 | Kud et al. | 528/292 |
| 5,512,699 | 4/1996 | Connor et al. | 564/153 |
| 5,534,197 | 7/1996 | Scheibel et al. | 510/356 |
| 5,669,984 | 9/1997 | Scheibel et al. | 134/25.2 |
| 5,681,803 | 10/1997 | Okano et al. | 510/130 |
| 5,777,046 | 7/1998 | Boeckh et al. | 525/444 |

FOREIGN PATENT DOCUMENTS

| | | |
|---|---|---|
| 689649 | 5/1996 | Australia . |
| WO 92/17523 | 10/1992 | WIPO . |
| WO 95/02029 | 1/1995 | WIPO . |
| WO 95/02030 | 1/1995 | WIPO . |
| WO 95/19953 | 7/1995 | WIPO . |
| WO 95/19955 | 7/1995 | WIPO . |
| WO 95/20026 | 7/1995 | WIPO . |
| WO96/14926 | 5/1996 | WIPO . |

OTHER PUBLICATIONS

Milton J. Rosen, "Geminis: A New Generation of Surfactants," Chemtech, Mar. 1993, pp. 30–33.

V. P. Gorodnov and L. V. Mineev: "Synthesis and Study of Demulsifying Capabilities of Ethoxylated Ethylenediamides of Fatty Acids." Translated from Khimiya i Tekhnologiya Topliv i Masel, No. 3, pp. 33–36, Mar. 1973.

*Primary Examiner*—Yogendra Gupta
*Assistant Examiner*—Charles Boyer
*Attorney, Agent, or Firm*—Browning Bushman

[57] ABSTRACT

The present invention relates to the use of anionic gemini tensides of the formula (I)

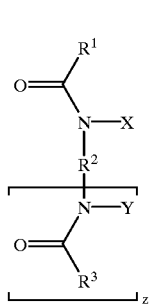

(I)

in which $R^1$ and $R^3$ are, mutually independently, a hydrocarbon radical with 1 to 22 carbon atoms, $R^2$ is a spacer containing 0 to 100 alkoxy groups, and X and Y, mutually independently, are functional groups and the degree of substitution Z=1 to 10, in washing, cleaning and body care agents in which the proportion of said tensides amounts to at least 0.1%.

15 Claims, No Drawings

USE OF ANIONIC GEMINI TENSIDES IN FORMULATIONS FOR WASHING, CLEANING AND BODY CARE AGENTS

The invention relates to the use of anionic gemini surfactants of the formula (I) in formulations for the washing and cleaning of textiles, the cleaning of hard surfaces and the cleansing and washing of skin and hair.

The putting together of formulations for detergents, cleaning products and body care compositions is a complex task, since the formulations must be capable of removing a wide variety of types of soiling from very different surfaces. The rapid and efficient removal of fatty or oily soiling generally poses a particular problem. In addition to the exclusively performance-related requirements, the ecotoxicological requirements placed on formulations for detergents, cleaning products and body care compositions are becoming ever more stringent.

The sparing use of natural resources is associated not just with the use of surfactants based on renewable raw materials but also, quite particularly, with the preparation of formulations which are ever more effective at a given level of raw materials use and which nevertheless satisfy the requirements of biodegradability and mildness to the skin. Furthermore, the surfactant-containing formulations for detergents and cleaning products, which are becoming ever more compact, must also be rapidly soluble in water in the washing liquor even with an amount of water which—again on ecological grounds—is falling.

The totality of these requirements can no longer be met purely by physical means, but instead requires the use of more powerful surfactants. The gemini, or twin, surfactants, hailed as a new generation of surfactants (M. J. Rosen, Chemtech, No. 3 (1995) 30), are surfactants which, insofar as their structure is optimized, possess markedly higher performance than their conventional equivalents and in addition offer—given the choice of the correct structural variant—a high degree of multifunctionality, thereby helping to increase the washing and/or cleaning power per unit mass of the formulation.

The gemini polyhydroxy- and gemini polyether-fatty acid amides described in the applications WO 95/19953 and WO 95/19955 are nonionic gemini surfactants. In comparison with the nonionic surfactants known today, however, these compounds do not offer any particular increase in efficiency per unit mass deployed. Also, the multifunctionality of these compounds can only be achieved by a substantial increase in the molecular mass, a fact which from the standpoint of protecting the ecosystem must be regarded as rather counterproductive.

If, however, anionic gemini surfactants are employed, as described in DE-A 44 40 328 (formula I), there is a significant increase in the efficiency of overall end formulations. This is possible because the anionic gemini surfactants are markedly more efficient than conventional anionic surfactants in terms, for example, of critical micelle concentration, surface tension, solubility in water, stability to hardness, solubilizing effect and washing power, and, furthermore, owing to their particular structure, are particularly mild to the skin and biodegradable.

Formula (I):

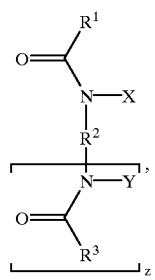

The invention therefore provides for the use of at least 0.1% of anionic gemini surfactants of the formula (I) in detergents, cleaning products and body care compositions, where $R^1$ and $R^3$ independently of one another are each an unbranched or branched, saturated or unsaturated hydrocarbon radical having 1 to 22, preferably 7 to 17, carbon atoms, and $R^2$ is a spacer consisting of an unbranched or branched chain having 2 to 100 carbon atoms which comprises 0 to 20 oxygen atoms, 0 to 20 nitrogen atoms, 0 to 4 sulfur atoms and/or 0 to 3 phosphorus atoms and has from 0 to 20 functional side groups such as, for example, hydroxyl, carbonyl, carboxyl, amino and/or acylamino groups and the spacer comprises from 0 to 100, preferably from 0 to 20, alkoxy groups, X and Y independently of one another are functional groups and the degree of substitution z is from 1 to 10. A detailed description of various embodiments of the spacer is contained in German Patent Application 44 40 328, which we hereby incorporate by reference.

X or Y is a substituent of the formula II $$—(C_2H_4O)_\alpha(C_3H_6O)_\beta H \qquad (II)$$

where $\alpha=0$ to 50, preferably $\alpha=10$ to 30, $\beta=0$ to 60, preferably $\beta=20$ to 40, and $\alpha+\beta=1$ to 100, preferably $\alpha+\beta=10$ to 50, and $R^2$ is not $C_2H_4$ if $\beta=0$, and X and Y are a substituent of the formula (III) or X and Y are, independently of one another, substituents of the formula III $$—(C_2H_4O)_\gamma(C_3H_6O)_\delta—FR \qquad (III)$$

where in each case $\gamma=0$ to 20, preferably $\gamma=0$ to 8, $\delta=0$ to 20, preferably $\delta=0$ to 12, and $\gamma+\delta=1$ to 40, preferably $\gamma+\delta=5$ to 20, where the alkoxide units are incorporated randomly or in blocks and the sequence is arbitrary, and where FR is a functional radical —$CH_2$—COOM, —$SO_3M$, —$P(O)(OM_2)$, —$C_2H_4$—$SO_3M$ or —O—C(O)—$C_2H_3(SO_3M)$—$CO_2M'$ where M, M'=an alkali metal, ammonium, alkanolammonium or ½ alkaline earth metal ion.

The degree of alkoxylation is an average in each case and can adopt any desired value—including a nonintegral value—within the stated limits.

In addition to at least 0.1% of anionic gemini surfactant of the formula (I), which can be present as a mixture of different homologs of the same basic structure (both in terms of the carbon chain length of the lipophilic chains and also of the spacer or of the alkoxyether chains) and as a mixture of compounds having different degrees of functionality, for example a degree of sulfation of between 1 and 2, the novel formulations for detergents, cleaning products and body care compositions may also include in each case at least 0.001%, preferably at least 0.1%, of one or more detergent, cleaning product or body care composition components, which are set out in more detail below. All percentages are to be understood as by weight unless related explicitly to a different variable. Such components are as follows:

a) Enzymes: A whole range of enzymes can be present in the novel formulations, for example proteases, amylases, lipases, cellulases and peroxidases and mixtures of the respective enzymes. Other enzymes too can be incorporated into the detergent formulations, and may—like the above—have a wide variety of origins, from bacteria, fungi, for example yeasts, and other plants, and may also be of animal origin.

Various factors determine the choice of individual enzymes, such as for example the optimum pH activity and/or pH stability, the thermal stability, the stability to various surfactants, builders, etc. Enzymes are employed in amounts of up to 50 mg, preferably from 0.01 mg to 3 mg of active enzyme per gram of detergent formulation, i.e. from 0.001% to about 5% in the detergent formulations. For proteases the concentration for use is governed by an activity of from 0.005 to 0.1 Anson Units (AU) per gram of formulation.

b) Enzyme stabilizers: These include water-soluble sources of calcium ions and/or magnesium ions, which must frequently be added so that the builder system does not remove these central atoms from the enzymes as well and thus deactivate them. In this context, calcium ions are generally more effective than magnesium ions. Additional stabilization can be effected by the addition of borates (e.g., U.S. Pat. No. 4,537,706, Severson). The formulations typically contain from 1 to 30, preferably from 2 to 20, particularly preferably from 5 to 15 and, with very particular preference, from 8 to 12 millimoles of calcium ions per liter of final formulation.

Although the concentration in various formulations can vary in dependence on the enzymes used, there should always be sufficient calcium ions available, after complexing by the builder system and by soaps, to keep the enzymes activated. Any water-soluble calcium or magnesium salt can be used, examples (without limiting the novel formulations thereto) being: calcium chloride, formate, sulfate, hydroxide, malate, maleate, acetate and the corresponding magnesium salts. Depending on the nature and amount of the enzymes used the detergent formulations contain from 0.05% to 2% of water-soluble calcium and/or magnesium salts.

Borate stabilizers are present in the formulations in proportions of from 0.25% to 10%, preferably from 0.5% to 5% and, with particular preference, from 0.75% to 3%, calculated as boric acid. The borate stabilizers added must be able to form boric acid. In this case the direct use of boric acid is preferred, although with no limitation it is possible to employ boron oxide, borax, other alkali metal borates and substituted boric acids, for example phenyl-, butyl- and p-bromophenylboric acid.

c) Bleaching systems—bleaches and bleach activators: For the novel formulations the use of a bleaching system, whether comprising both bleach and bleach activator or just a bleach, is optional. If used, the bleaches are employed in amounts of from 1 to 30%, preferably from 5 to 20%. If employed, bleach activators are used in amounts of from 0.1 to 60% of the bleach. It is preferred to employ from 0.5 to 40% of bleaching system, based on the formulation. All bleaches suitable for the cleaning of textiles, hard surfaces (industrial and household cleaners, rinse aids) or other cleaning tasks can be employed. These include both bleaches operating on an oxygen basis and other systems. Perborates, for example sodium perborates, whether as mono- or tetrahydrate, can be employed, as can percarboxylic acid bleaches and their salts. Appropriate representatives of this class include magnesium peroxyphthalate hexahydrate, magnesium metachloroperbenzoate, 4-nonylamino-4-oxoperoxybutanoic acid, diperoxydodecanedioic acid and, with particular preference, 6-nonylamino-6-oxoperoxycapric acid (U.S. Pat. No. 4,634, 551, Burns et al.). Peroxygen bleaches can likewise be employed. Appropriate representatives of this class include sodium carbonate peroxohydrate and comparable percarbonates, sodium pyrophosphate peroxohydrate, urea peroxohydrate, sodium peroxide and persulfate bleaches. Mixtures of bleaches can also be employed in the novel detergent and cleaning product formulations.

Peroxygen bleaches are preferably combined with bleach activators, the latter including—without restricting the novel formulations thereto—nonanoyloxyphenylsulfonate, tetraacetylethylenediamine and mixtures thereof and also other bleach/bleach activator combinations mentioned in U.S. Pat. No. 4,634,551. Very particularly preferred bleach activators are amide derivatives of the formula $R^1N(R^5)C(O)R^2C(O)L$ or $R^1C(O)N(R^5)R^2C(O)L$, in which $R^1$ is an alkyl group having 6 to 12 carbon atoms, $R^2$ is an alkylene group having 1 to 6 carbon atoms, $R^5$ is a hydrogen atom or is alkyl, aryl or alkylaryl having 1 to 10 carbon atoms and L is any leaving group which is suitable for nucleophilic reactions (for example, phenylsulfonate). Examples which may be mentioned here are the following compounds: (6-octanamidocaproyl)oxyphenylsulfonate, (6-nonanamidocaproyl)oxyphenylsulfonate, (6-decanamidocaproyl)oxyphenylsulfonate and mixtures thereof. Acyllactam activators belong to another class of preferred bleach activators, especially acylcaprolactam and acylvalerolactam having alkyl-, aryl-, alkoxyaryl- and alkylaryl-acyl groups containing 1 to 16 carbon atoms. The bleaches not based on oxygen include sulfonated zinc- and/or aluminum-phthalocyanines among the preferred systems.

d) Builder systems: Likewise optionally, the novel detergents and cleaning products may include builder systems (total builders) consisting of water-softening silicates and other organic and/or inorganic builders. They are employed in detergent formulations in order to support the removal of particulate dirt and to control the water hardness. Liquid formulations contain from 0 to 50%, preferably from 5 to 50% and, with particular preference, from 5 to 30% of total builders. Granular formulations contain from 0 to 80%, preferably from 10 to 80% and, with particular preference, from 15 to 50% of total builders. However, there is no intention here to exclude higher concentrations.

The inorganic builders include, in particular, silicates and alumosilicates. Examples of silicate builders are alkali metal silicates, especially those with $SiO_2:Na_2O$ in a ratio of from 1.6:1 to 3.2:1, and phyllosilicates, such as sodium silicates of the type $NaMSi_xO_{2x+1} \cdot yH_2O$ (M is Na or H, x=1.9–4, y=0–20). Particular preference is given to the type designated SKS-6. Magnesium silicates can also be employed here. Alumosilicates are likewise useful in the novel formulations and are particularly important in granular detergent formulations. The alumosilicate builders that can be used can be described by the empirical formula $[M_z(zAlO_2)_y]\cdot xH_2O$, where z and y adopt values of at least 6, the molar ratio of z to y is in the range from 1.0 to 0.5, and x adopts values from about 0 to 30. The alumosilicates can be either crystalline or amorphous, synthetic or naturally occurring. The proportion of silicate builders can be from 0 to 60%.

Without limiting the formulations thereto, the inorganic builders also include alkali metal salts, ammonium salts and alkanolammonium salts of polyphosphates (for example, tripolyphosphates, pyrophosphates and polymeric metaphosphates), phosphonates, carbonates (including bicarbonates and sesquicarbonates) and sulfates.

Organic builders too are among the builders which can be used. They include polycarboxylates, such as ether carboxylates (cyclic or noncyclic), hydroxypolycarboxylates, copolymers of maleic anhydride and ethylene or vinyl methyl ether, 1,3,5-trihydroxybenzene-2,4,6-trisulfonic acid and carboxymethoxysuccinic acid, all of which can be employed in the form of the acid or its alkali metal, ammonium or organoammonium salts. Alkyl salts, ammonium salts or organoammonium salts of polyacetic acid are likewise suitable, as are salts of citric acid or combinations of various builders. Alkenylsuccinic acids and salts are particularly preferred organic builders. Monocarboxylic acid salts can likewise be incorporated into the formulations, either alone or in combination with one of the abovementioned builders.

The inorganic builders (excluding silicates) and/or organic builders are present in proportions of from 0 to 40%.

e) Soil release polymers: All prior art soil release polymers can be employed as ingredients in the novel formulations. As a constituent of formulations, soil release polymers contribute to more ready detachment of oil and fat soiling, especially during washing operations and in the finishing of textiles. A feature of soil release polymers is that they have both hydrophilic and hydrophobic structural units. The mode of action of soil release polymers is based on the modification of the fiber surface of polyester fabrics or cotton/polyester blend fabrics with the aid of the hydrophilicizing polymer. In this context, the hydrophilic segment of the soil release polymer brings about more ready wetting of the surface, while the hydrophobic segment functions as an anchor group.

Moisture transport (water absorption and wicking) is considerably improved in the case of the hydrophobic fabrics, such as polyester or polyester/cotton blends, treated with the soil release polymer. They also give the materials antistatic and slip properties, thereby facilitating the handling of these fibers on cutting and sewing (textiles processing). The treatment of the fabric with the soil release polymer is to be understood as a kind of impregnation; in other words, the soil release polymer remains on the fiber for a number of washing cycles.

The most important group of soil release polymers includes polyesters and oligoesters based on terephthalic acid/polyoxyalkylene glycols/monomeric glycols. Soil release polymers of this group have been on the market for a number of years already. The principal commercial products include ZELCON (Du Pont), MILEASE T (ICI), ALKARIL QCF/QCJ (Alkaril Inc.) and REPEL-O-TEX (Rhone-Poulenc). In the context of this invention, preference is given to soil release polymers that can be described by the following empirical formula:

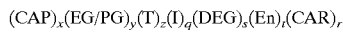

In this formula (CAP) represents "capping groups", which cap the polymer at the end. End group capping contributes to stabilizing the polymers. (CAP) stands for a large number of possible end groups. Preferred end groups include sulfoaroyl groups, for example the sulfobenzoyl group, which can be introduced in the form of a transesterification with alkyl sulfobenzoate. The incorporation of end groups firstly has a regulating effect on the molecular weight and secondly leads to stabilization of the polymers obtained. In addition to sulfoaroyl groups it is also possible to employ ethoxylated or propoxylated hydroxyethane- and hydroxypropanesulfonates, as are described, for example, in WO 95/02029 and WO 95/02030.

Other preferred end groups are poly(oxyethylene) monoalkyl ethers in which the alkyl group contains 1 to 30 C atoms and the polyoxyethylene group consists of 2–200 oxyethylene units. End groups of this kind are described, for example, in WO 92/17523 and DE 40 01 415. EP 0 253 567 and EP 0 357 280 describe, in particular, those end-group-capped polyesters which are capped both by nonionic groups, such as C1–C4-alkyl, C1–C4-hydroxyalkyl and C1–C4-acyl, and by ionic succinate groups. Also possible in principle are mixtures of different end groups, in which case x adopts values of 0–2.

The group (EG/PG) stands for an oxyethyleneoxy or oxypropyleneoxy group or mixtures thereof, where y adopts numerical values from 0 to 80. A variant of the abovementioned polyesters described involves the introduction of branched monomeric glycol units, such as 1,2-butylene glycols and 3-methoxy-1,2-propylene glycols (EP 0 241 985).

The group (T) stands, inter alia, for a terephthaloyl group which functions in the polymer, so to speak, as an anchor group between soil release polymer and substrate (fiber). With all prior art oligoesters- or polyester-based soil release polymers, the presence of terephthaloyl groups is essential for the performance of said additive. In addition to terephthaloyl groups, however, it is also possible for aliphatic analogs to be present, for example adipates, which can be incorporated by way of adipic acid or adipic diesters. DE 44 03 866, for example, claims amphiphilic polyesters which include not only aromatic but also aliphatic dicarboxylic acids and can be employed as a detergent additive or soil release polymer. In that case z adopts values from 1 to 50.

Each (I) is an internal anionic group where q=0–30. The incorporation of anionic groups, primarily sulfoisophthaloyl groups, into the polymer framework proves to be highly advantageous for the performance of the soil release polymer. The sulfoisophthaloyl groups stabilize the polymer and inhibit the transition from the desired amorphous form of the polymer to its less readily soluble crystalline form. U.S. Pat. No. 4,427,557 and EP 0 066 944 describe those anionic modifications of the abovementioned polyesters that include, as a further polymerization component, the sodium salt of sulfoisophthalic acid. The polymerized polyethylene glycols (PEGs) possess molar masses of 200–1000 and, following their polymerization with ethylene glycol and terephthalic acid, produce polyesters having molar weights of 2000–10,000.

DEG is a di(oxyethylene)oxy group where s=0–80.

Each (En) is a poly(oxyalkylene)oxy group which is composed of from 2 to 100 oxyalkylene groups, for which t is 0–25, and the alkyl groups contain 2–6 C atoms. In the majority of cases these poly(oxyalkylene)oxy groups are poly(oxyethylene)oxy groups, with considerable variation possible in the molecular weights. In addition to poly (oxyethylene)oxy groups it is also possible for poly (oxypropylene)oxy groups, and all conceivable mixtures, to be present as well. DE 14 69 403, for example, describes a process for the surface-modifying treatment of articles derived from polyesters. There, the polyesters prepared are composed of ET units with ET:POET=2–6:1, using polyethylene glycols having molar weights of 1000–4000. U.S. Pat. No. 3,959,230 claims ET/POET polyesters with ET:POET=25:75–35:65, where low molecular mass polyethylene glycols having molar weights of 300–700 are employed and the polyesters obtained have molar weights of 25,000–55,000.

Each (CAR) is a carbonyl group (C=O) of a carbonate unit, where r is a number from 0 to 80. It is found that by incorporating carbonate groups, in the form of carbonic esters, into the polymer framework it is possible to increase further the performance of the soil release polymers. On the one hand, polymers of this type can be dispersed more readily; on the other hand, it is possible with the aid of carbonic esters to obtain flowable, pumpable polymers, which brings with it considerable advantages in the context of the usual formulating operation.

The polyester- or oligoester-based soil release polymers described by the above empirical formula possess molecular weights between 200 and 100,000. Preference is usually given to molecular weights in the range from 500 to 25,000.

In addition to this class of soil release polymers it is also possible, within the scope of the formulations, to employ cellulose derivatives. Such products are obtainable commercially, for example, as hydroxy ethers of cellulose under the product name METHOCEL (Dow). Preferred cellulose derivatives are those with C1–C4-alkyl- and C4-hydroxyalkyl celluloses (U.S. Pat. No. 4,000,093). A further group of soil release polymers which can be employed are poly(vinyl ester) compounds. Among these, graft polymers of polyvinyl acetate and polyoxyethylene glycol are particularly preferred. Products of this kind are on the market, such as SOKALAN HP 22 (BASF), for example.

Where soil release polymers are employed in the novel formulations, the content is from 0.01 to 10.0% by weight. Preference is given to a content of from 0.1 to 5% by weight, based on the corresponding formulation.

f) Chelating agents: The novel formulations may optionally also include agents which complex iron ions and manganese ions by forming chelates, and which belong to the group of the aminocarboxylates, aminophosphonates and polyfunctionalized aromatic compounds (for example, dihydroxybenzenesulfonic acid derivatives). Mixtures of different chelating agents are also effective. A preferred biodegradable chelating agent is ethylenediamine disuccinate. The abovementioned agents are employed in proportions of from 0.1 to 10%, preferably from 0.1 to 3.0%, of the detergent formulation.

g) Components for removing clay or loam dirt and preventing resoiling: For this purpose the novel formulations can include alkoxylated, preferably ethoxylated, amines, irrespective of whether these are mono-, oligo- or polymeric amines. For solid formulations the amount used is from 0.01 to 10%, for liquid formulations from 0.01 to 5%, of the overall formulation. Other groups of compounds exhibiting these properties are cationic compounds (as in EP-A-0 111 984), zwitterionic polymers (as in EP-A-0 112 592) or carboxymethylcellulose, which are likewise able to increase the soil-bearing capacity of a wash liquor.

h) Polymeric dispersion aids (cobuilders): These additives are employed in amounts of from 0.1 to 7.0% of the novel formulation as a whole and are polycarboxylates or polyethylene glycols which not only strengthen the action of the builder employed but also prevent instances of encrustation and resoiling and play a part in detaching particulate dirt. The compounds which can be employed here are obtained by addition polymerization or copolymerization of appropriate unsaturated carboxylic acid monomers or carboxylic anhydride monomers. Preference is given here to polyacrylates, but also to maleic anhydride-acrylic acid copolymers. The molecular weights of the former are in a range from 2000 to 10,000, preferably from 4000 to 7000 and, with particular preference, in the range from 4000 to 5000. Suitable copolymers have molar weights of from 2000 to 100,000, preferably from 5000 to 75,000 and, with particular preference, from 7000 to 65,000. Polyethylene glycols that can be used have molar weights in the range from 500 to 100,000, particularly preferably from 1500 to 10,000. Polyaspartates and polyglutamates can also be employed together with zeolite builders, the polyaspartates that can be used having average molar weights of about 10,000.

i) Fluorescent whitening agents: All prior art fluorescent whiteners can be employed in the novel formulations. They are incorporated in proportions of from 0.05 to 1.2%, based on the overall formulation. Some nonlimiting examples of appropriate compound groups that may be mentioned are stilbene derivatives, pyrazolines, coumarin, carboxylic acids, methinecyanines, dibenzothiophene 5,5-dioxide, azoles, and 5- and 6-membered heterocycles.

j) Foam inhibitors: Depending on the exact composition (i.e. foaming power of the surfactants used) and the nature of the foam inhibitor it is necessary to employ from 0 to 5% (based on overall formulation) thereof. Mono-fatty acid salts are employed in an amount of from 0 to 5%, preferably from 0.5 to 3%, silicones in an amount of up to 2%, preferably from 0.01 to 1% and, with particular preference, from 0.25 to 0.5%. Compounds which can be employed as foam inhibitor in the novel formulations include mono-fatty acids and their salts having carbon chain lengths of from 10 to 24, preferably from 12 to 18, carbon atoms. It is also possible to employ compounds of high molecular mass which are not surface-active, such as paraffins, fatty acid esters (for example, triglycerides), aliphatic ketones, N-alkylated aminotriazines, di- to tetraalkyldiaminechlorotri-azines, monostearyl phosphates and monostearyl alcohol phosphate esters. Mixtures of silicones and silane-modified silicates, generally with polyalkylene glycols as solvents can also be employed as foam inhibitors.

k) Textile softeners: Various textile softeners which can be used in the washing process can be employed here, but especially smectite clays and other softening clays in amounts of between 0.5 and 10% (based on the overall formulation). These softeners can be used in combination with other softeners, such as amines and the widespread cationic softeners.

l) Surfactants: In addition to the anionic gemini surfactants of the formula (I) it is possible to combine in each case combinations or individuals among the surfactants mentioned below with the gemini surfactants in the novel formulations. In this case from 0.1 to 70% of these surfactants is employed. Without limiting the formulations thereto, possible examples of nonionic surface-active substances are fatty acid glycerides, fatty acid polyglycerides, fatty acid esters, alkoxylates of $C_6$–$C_{30}$ alcohols, alkoxylated fatty acid glycerides, polyoxyethylene-oxypropylene glycol fatty acid esters, polyoxyethylenesorbitan fatty acid esters, polyoxyethylene-castor oil or hydrogenated castor oil derivatives, polyoxyethylene-lanoline derivatives, polyoxyethylene-fatty acid amides, polyoxyethylenealkylamines, derivatives of alkanolamines, derivatives of alkylamines, alkylamine oxides, derivatives of protein hydrolysates, hydroxy mixed ethers, alkyl polyglycosides and alkylglucamides (for example N-methyl alkylglucamides) and also nonionic gemini surfactants, or bridged nonionic surfactants (as described in WO 95/19951 (polyhydroxyamine compounds), WO 95/19953, WO 95/19954 and WO 95/19955 and also WO 95/20026).

Examples of anionic surface-active substances which can be employed for combinations are soaps, ethercarboxylic acids and their salts, alkylsulfonates, α-olefinsulfonates, α-sulfo-fatty acid derivatives (including those described in WO 93/25646), sulfonates of higher fatty acid esters, higher alcohol sulfates (primary and secondary), alcohol ether sulfates, hydroxy mixed ether sulfates, sulfates of alkoxylated carboxylic acid alkanolamides, salts of phosphate esters, taurides, isethionates, linear alkylbenzenesulfonates, bridged alkylbenzenesulfonates (such as DOWFAX types from Dow), alkylarylsulfonates, sulfates of polyoxyethylene-fatty acid amides and derivatives of acylamino acids, alkyl ether carboxylic acids, alkyl and dialkyl sulfosuccinates, alkenyl sulfosuccinates, alkyl or alkenyl sarcosinates and sulfated glycerol alkyl ethers.

Examples of common cationic surface-active substances that can be employed for combinations are alkyltrimethylammonium salts, dialkyldimethylammonium salts, alkyldimethylbenzylammonium salts, imidazolinium derivatives, alkylpyridinium salts, quaternized fatty acid esters of alkanolamines, alkylisoquinolinium salts, benzethonium chlorides and cationic acylamino acid derivatives.

Examples of surface-active substances which are ampholytes and betaines and can be employed for combinations are carbobetaines, for example cocoacylamidopropyldimethyl betaine, acylamidopentanediethyl betaine, dimethylammoniohexanoate-acylamidopropane- (or -ethane-)dimethyl (or -diethyl) betaine—all with carbon chain lengths of between 10 and 18, sulfobetaines, imidazoline derivatives, soya oil lipids and lecithin. The abovementioned amine N-oxides can also be in polymeric form, in which case the ratio of amine to amine N-oxide must be from 10:1 to 1:1,000,000. The average molar mass is from 500 to 1,000,000, particularly preferably from 5000 to 100,000.

m) Further components: Further components can be incorporated into the formulations of the detergents, cleaning products or body care compositions: further carriers, hydrotropic agents, processing auxiliaries, dyes or pigments, fragrances, solvents for liquid formulations (particular preference is given to alcohols having 1 to 6 carbon atoms and 1 to 6 hydroxyl groups), solid fillers for bar soap formulations, pearlescence agents, for example distearoyl glycerides, preservatives, buffer systems and so on. Should a relatively high foaming power of the formulation be required, as for example in some body care compositions, this power can be increased by, for example, adding $C_{10}$–$C_6$-alkanolamides (in concentrations of from 1 to 10% of the overall formulation). Further water-soluble magnesium salts can also be added to increase the foaming power and the fat-dissolving power, in amounts of from 0.1 to 2%.

If necessary, some of the abovementioned surfactant components can also be incorporated into the formulation in a form in which they are stabilized by adsorption on porous hydrophobic substances and sealed with a further hydrophobic coat.

Use: The formulations according to the invention can be used very widely; for example, as a skin cleanser, bath additive, shower product, denture cleanser, shampoo and conditioner, shaving soap, pre-shave product, disinfectant, dispersant, all-purpose detergent and light-duty detergent, and also in liquid form or else as a powder or granules, for textiles, washing-up products and dishwasher rinse aids, household cleaners and industrial cleaners.

EXAMPLES

The following examples, which are not intended to limit the claims in any way, show the positive performance properties of the gemini surfactants of formula (I), which predestine them for use in the abovementioned applications.

A) Cleaning of Hard Surfaces

To determine the cleaning action on hard surfaces, 7 carrier strips of rigid PVC (455×39×2.5 mm) were placed closely adjacent to one another. A white PVC film (400×400 mm) was placed without bubbles on one side of the carrier strips. Then PVC templates (300×350×3 mm) with a 260× 280 mm cutout were placed on the film in such a way that the cutout was over the center of the film. Within the area of the cutout, 2 g of a test soiling composition (7% by weight special black 4, from Degussa, 17% by weight of Myritol 318, from Henkel, 40% by weight of process oil 310, from Esso, 36% by weight of Exxon DSP 80/100, from Exxon) were distributed over the film using a flat brush. The carrier strips were cut with a knife. Each test strip was then placed in the metal guide rail of a Dardner washability and abrasion tester (model M-105-A, from Erichsen) and was cleaned with a damp sponge, located in a carriage, using 16 ml of the surfactant-containing formulation under test (surfactant content: 1% by weight). Cleaning took place by 10 back-and-forth passages of the carriage. After the test strips had been dried, the PVC film was detached from the carrier strip and bonded to white card with the cleaned side upward. The cleaning power of each of the surfactant-containing formulations was determined by spectrophotometry using a "datacolor 3890" spectrophotometer at a wavelength of 560 nm relative to a white standard (=100%) and a soiled standard (=0%).

Comparative Example

As a standard formulation, the cleaning power of a commercial all-purpose cleaner was determined as being 65%.

Examples according to the invention:

The cleaning powers of the novel anionic gemini surfactants were determined on the basis of the following formulation:

anionic gemini surfactant: 3.0% by weight
MARLIPAL 0 13/80*: 1.0% by weight
Coconut fatty acid Na salt: 0.24% by weight
*) $C_{13}$ alcohol with 8 ethylene oxide units (from Hüls).
The following anionic gemini surfactants were tested:
1: As formula (I) with $R^1=R^3=C_7$–$C_9$-alkyl, $R^2=C_6H_{12}$, $X=Y=(C_2H_4O)_{a,b}$, $SO_3Na$, a+b=8, z=1;
2: As formula (I) with $R^1=R^3=C_7$–$C_9$-alkyl, $R^2=C_6H_{12}$, $X=Y=(C_2H_4O)_{a,b}$, $SO_3Na$, a+b=20, z=1;
3: As formula (III) with $R^1=R^3=C_7$–$C_9$-alkyl, $R^2=C_2H_4$, $X=Y=(C_2H_4O)_{a,b}$, $SO_3Na$, a+b=16, z=1;

Example 1

The cleaning power of the formulation containing compound 1 was determined as being 72% and is therefore higher than that indicated in the comparative example.

Example 2

The cleaning power of the formulation containing compound 2 was determined as being 74% and is therefore higher than that indicated in the comparative example.

Example 3

The cleaning power of the formulation containing compound 3 was determined as being 66% and is therefore higher than that indicated in the comparative example.

B) Washing Power on Textiles

To determine the washing power on textiles, the drum of a commercial domestic washing machine was charged with 4 kg (for washing at 95° and 60° C.) or with 1 kg (for the 30° C. wash) of clean cotton ballast fabric from Carl Laarmann (Art. No 5005 HE). Furthermore, test swatches from WFK-Testgewebe GmbH soiled with skin grease pigment with the soiled side upward were sewn onto a white cotton towel (from Carl Laarmann, Art. No.: HL DIN G 25). Thus furnished, the cotton towel was placed in the drum of the domestic washing machine with the ballast fabric. The following WFK test fabrics were used:

Cotton (BW): 10 D

Cotton/polyester blend (MG): 20 D

Polyester (PE): 30 D

The washing powers of the novel anionic gemini surfactants were determined on the basis of the following formulation of a liquid heavy-duty detergent:

| | |
|---|---|
| Anionic gemini surfactant | 13.0% by weight |
| MARLIPAL 24/70*[1] | 15.5% by weight |
| KOH, 50% strength | 3.9% by weight |
| Coconut fatty acid | 10.0% by weight |
| Triethanolamine | 5.0% by weight |
| 1,2-Propylene glycol | 3.0% by weight |
| Ethanol | 8.0% by weight |
| Dequest 2060 S*[2] | 1.5% by weight |
| Remainder to 100% by weight water | |

*[1]$C_{12/14}$ alcohol with 7 ethylene oxide units (from Hüls)
*[2]Diethylenetriaminepenta(methanephosphonic acid) (from Monsanto)

The amount of liquid heavy-duty detergent used was 25 g per wash. After washing, the WFK test fabrics were dried.

The washing power was determined by spectrophotometry by measuring the reflectance with the aid of a datacolor 3890 spectrometer (white standard: 100% reflectance, soiled fabric: 0% reflectance).

The following anionic gemini surfactants were tested:

4: As formula (I) with $R^1=R^3=C_7-C_9$-alkyl, $R^2=C_4H_8$, $X=Y=(C_2H_4O)_{a,b}$, $(SO_3Na)_{1.16}$, a+b=17.3, z=1;

5: As formula (I) with $R^1=R^3=C_{11}-C_{13}$-alkyl, $R^2=C_6H_{12}$, $X=Y=(C_2H_4O)_{a,b}$, $(SO_3Na)_{1.65}$, a+b=17.9, z=1;

In order that the washing power could be better assessed, in place of the gemini surfactants the commonly used MARLON PS (sec-alkanesulfonate Na salt, Hüls AG) was employed in the above formulation at the same concentration.

Reflectances found, in %:

| Surfactant used in the formulation | PE 30° C. | MG 30° C. | MG 60° C. | BW 60° C. | BW 95° C. |
|---|---|---|---|---|---|
| sec-alkanesulfonate Na salt (not according to the invention) | 49 | 44 | 30 | 24 | 25 |
| 4 | | 58 | 44 | 30 | 30 | 31 |
| 5 | | 52 | 48 | 33 | 30 | 40 |

It is found that 4 and 5 bring about equal or substantially better reflectances than does the sec-alkanesulfonate Na salt.

What is claimed is:

1. A detergent, cleaning product or body care composition using at least 0.1% by weight of anionic gemini surfactants of the formula I

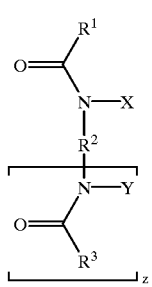

(I)

wherein $R^1$ and $R^3$ independently of one another are a hydrocarbon radical having 1 to 22 carbon atoms, $R^2$ is a spacer containing from 0 to 20 alkoxy groups, and one of X or Y is a substituent of the formula II $$—(C_2H_4O)_\alpha(C_3H_6O)_\beta H \quad (II)$$

wherein α=0 to 50, β=0 to 60, and α+β=1 to 100, and the other of X or Y is a substituent of the formula III or X and Y are, independently of one another, substituents of the formula III $$—(C_2H_4O)_\gamma(C_3H_6O)_\delta FR \quad (III)$$

wherein FR is a functional radical $—CH_2—COOM$, $—SO_3M$, $—P(O)(OM)_2$, $—O—C(O)—C_2H_3)—CO_2M'$ or $—C_2H_4—SO_3M$ wherein M, M'=an alkali metal ion, ammonium ion, alkanolammonium ion or ½ alkaline earth metal ion, wherein γ=0 to 20, δ=0 to 20, and γ+δ=1 to 40, and wherein the alkoxide units in the compounds of the formulae II and III are incorporated randomly or in blocks and the sequence is arbitrary, and wherein the degree of substitution Z is from 1 to 10.

2. A detergent, product or composition as claimed in claim 1, using at least 0.1% by weight of anionic gemini surfactants of the formula I, wherein the hydrocarbon radicals $R^1$ and $R^3$ independently of one another are an unbranched or branched, saturated or unsaturated hydrocarbon radical having 1 to 22 carbon atoms, $R^2$ is a spacer consisting of an unbranched or branched chain having 2 to 100 carbon atoms which comprises 0 to 20 oxygen atoms, 0 to 20 nitrogen atoms, 0 to 4 sulfur atoms and/or 0 to 3 phosphorus atoms and has from 0 to 20 hydroxyl, carbonyl, carboxyl, amino and/or acylamino groups.

3. A detergent, product or composition as claimed in claim 1 or 2, using at least 0.1% by weight of anionic gemini surfactants of the formula I, wherein the gemini surfactants, with the same basic structure, are a mixture of homologs having lipophilic hydrocarbon radicals which differ in length.

4. A detergent, product or composition as claimed in any of claims 1 or 2, using at least 0.1% by weight of anionic gemini surfactants of the formula I, wherein the gemini surfactants, with the same basic structure, as a mixture of homologs with spacers $R^2$ which differ in length.

5. A detergent, product or composition as claimed in any of claims 1 or 2, using at least 0.1% by weight of anionic gemini surfactants of the formula I, wherein the gemini surfactants, with the same basic structure, are a mixture of homologs with alkoxy chains which differ in length in the spacer $R^2$ and/or in the functional groups X and Y.

6. A detergent, product or composition as claimed in any of claims 1 or 2, using at least 0.1% by weight of anionic gemini surfactants of the formula I, wherein further anionic, nonionic, cationic, betaine and/or amphoteric surface-active compounds are present.

7. A detergent, product or composition as claimed in claim 6, using at least 0.1% by weight of anionic gemini surfactants of the formula I, wherein nonionic surface-active compounds employed are fatty acid glycerides, fatty acid polyglycerides, fatty acid esters, alkoxylates of $C_6$–$C_{30}$ alcohols, alkoxylated fatty acid glycerides, polyoxyethyleneoxypropylene glycol fatty acid esters, polyoxyethylenesorbitan fatty acid esters, polyoxyethylene-castor oil or hydrogenated castor oil derivatives, polyoxyethylene-lanoline derivatives, polyoxyethylene-fatty acid amides, polyoxyethylenealkylamines, derivatives of alkanolamines, derivatives of alkylamines, alkylamine oxides, derivatives of protein hydrolysates, hydroxy mixed ethers, alkyl polyglycosides, alkylglucamides, nonionic gemini surfactants and nonionic bridged surfactants and mixtures thereof.

8. A detergent, product or composition as claimed in claim 6, using at least 0.1% by weight of anionic gemini surfactants of the formula I, wherein anionic surface-active compounds employed are soaps, ethercarboxylic acids and their salts, alkysulfonates, α-olefinsulfonates, α-sulfo-fatty acid derivatives, sulfonates of higher fatty acid esters, higher primary and secondary alcohol sulfates, alcohol ether sulfates, hydroxy mixed ether sulfates, sulfates of alkoxylated carboxylic acid alkanolamides, salts of phosphate esters, taurides, isethionates, linear alkylbenzenesulfonates, bridged alkylbenzenesulfonates, alkylarylsulfonates, sulfates of polyoxyethylene-fatty acid amides and derivatives of acylamino acids, alkyl ether carboxylic acids, alkyl and dialkyl sulfosuccinates, alkyl or alkenyl sarcosinates and sulfated glycerol alkyl ethers and mixtures thereof.

9. A detergent, product or composition as claimed in claim 6, using at least 0.1% by weight of anionic gemini surfactants of the formula I, wherein cationic surface-active compounds employed are alkyltrimethylammonium salts, dialkyldimethylammonium salts, alkyldimethylbenzylammonium salts, imidazolinium derivatives, alkylpyridinium salts, quaternized fatty acid esters of alkanolamines, alkylisoquinolinium salts, benzethonium chlorides and cationic acylamino acid derivatives.

10. A detergent, product or composition as claimed in claim 6, using at least 0.1% by weight of anionic gemini surfactants of the formula I, wherein surface-active betaines and ampholytes employed are coco-acylamidopropyl betaine, acylamidopentenediethyl betaine, dimethylammoniohexanoate-acylamidopropane-(or-ethane-)dimethyl(or-diethyl) betaine with carbon chain lengths of from 10 to 18 carbon atoms, sulfobetaines, imidazoline derivatives, soya oil lipids and lecithin and mixtures thereof.

11. A cleaning product for textiles, using at least 0.1% by weight of anionic gemini surfactants of the formula I as set forth in any of claims 1 or 2.

12. A cleaning product for hard surfaces, using at least 0.1% by weight of anionic gemini surfactants of the formula I as set forth in any of claims 1 or 2.

13. A manual-rinsing product using at least 0.1% by weight of anionic gemini surfactants of the formula I as set forth in any of claims 1 or 2.

14. A cleansing product for skin and hair, using at least 0.1% by weight of anionic gemini surfactants of the formula I as set forth in any of claims 1 or 2.

15. A body care composition using at least 0.1% by weight of anionic gemini surfactants of the formula I as set forth in an of claims 1 or 2.

* * * * *

UNITED STATES PATENT AND TRADEMARK OFFICE
CERTIFICATE OF CORRECTION

| | |
|---|---|
| PATENT NO. : 6,156,721 | |
| DATED : December 5, 2000 | |
| INVENTOR(S) : Klaus Kwetkat, Michael Brock, and Herbert Koch | |

It is certified that error appears in the above-identified patent and that said Letters Patent is hereby corrected as shown below:

Column 12,
Line 60, delete "as" and insert therefor -- are --.

Column 14,
Line 34, delete "an" and insert therefor -- any --.

Signed and Sealed this

Second Day of October, 2001

*Attest:*

*Attesting Officer*

NICHOLAS P. GODICI
*Acting Director of the United States Patent and Trademark Office*